United States Patent
Naka et al.

(10) Patent No.: US 8,796,033 B2
(45) Date of Patent: Aug. 5, 2014

(54) METHOD OF DETERMINING MINUTE AMOUNTS OF ADDITIVES IN POLYMERS

(75) Inventors: Jiro Naka, Tokyo (JP); Hiroshi Kurokawa, Tokyo (JP); Junji Kobayashi, Tokyo (JP); Satoru Toyama, Tokyo (JP); Noriko Hirano, Tokyo (JP); Eiji Hara, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 2270 days.

(21) Appl. No.: 10/576,254

(22) PCT Filed: Oct. 14, 2004

(86) PCT No.: PCT/JP2004/015125
§ 371 (c)(1),
(2), (4) Date: Mar. 9, 2007

(87) PCT Pub. No.: WO2005/052552
PCT Pub. Date: Jun. 9, 2005

(65) Prior Publication Data
US 2010/0108875 A1 May 6, 2010

Related U.S. Application Data

(63) Continuation-in-part of application No. PCT/JP03/15090, filed on Nov. 26, 2003.

(51) Int. Cl.
*G01N 33/44* (2006.01)
*G01N 1/40* (2006.01)
*G01N 30/00* (2006.01)

(52) U.S. Cl.
CPC ...... *G01N 1/4055* (2013.01); *G01N 2001/4061* (2013.01); *G01N 33/442* (2013.01); *G01N 2030/009* (2013.01)
USPC .............................. 436/85; 436/164; 436/173

(58) Field of Classification Search
CPC ... C08L 2666/02; C08L 53/025; C08L 71/02; C08L 23/12; C08L 2201/02
See application file for complete search history.

(56) References Cited

U.S. PATENT DOCUMENTS

| 5,094,753 A | 3/1992 | Allington et al. |
| 5,160,624 A | 11/1992 | Clay et al. |

(Continued)

FOREIGN PATENT DOCUMENTS

| EP | 0 655 618 | 5/1994 |
| EP | 0 601 689 | 6/1994 |

(Continued)

OTHER PUBLICATIONS

Richter et al. "Accelerated Solvent Extraction: A Technique for Sample Preparation", Anal. Chem., 1996, v. 68, pp. 1033-1039.*

(Continued)

*Primary Examiner* — Yelena G Gakh
(74) *Attorney, Agent, or Firm* — Leydig, Voit & Mayer, Ltd.

(57) ABSTRACT

A method for analyzing a minute quantity of a material included in a different material is performed in short extraction treatment without taking a long time and the minute content is rapidly analyzed. The method of analyzing a minute content includes mounting on a sample table a sample piece of a material having a minute content of a different material to be analyzed; dropping onto the sample table a solvent for extracting the minute content from the sample piece, so that the solvent is disposed between the sample table and the sample piece; maintaining at room temperature the solvent between the sample table and the sample piece, and, with the solvent maintained between the sample table and the sample piece, extracting the material of the minute content from the sample piece; and analyzing the content extracted from the sample piece.

5 Claims, 23 Drawing Sheets

(56) References Cited

U.S. PATENT DOCUMENTS

| | | |
|---|---|---|
| 5,173,188 A | 12/1992 | Winter et al. |
| 5,250,195 A | 10/1993 | Winter et al. |
| 5,268,102 A | 12/1993 | Clay et al. |
| 5,268,103 A | 12/1993 | Jameson et al. |
| 5,269,930 A | 12/1993 | Jameson |
| 5,453,380 A | 9/1995 | Poole et al. |
| 5,635,070 A | 6/1997 | Allington et al. |
| 5,660,727 A | 8/1997 | Gleave et al. |
| 5,750,008 A | 5/1998 | Lautenschläger |
| 5,843,311 A | 12/1998 | Richter et al. |
| 5,858,178 A | 1/1999 | Lautenschläger |
| 5,932,095 A | 8/1999 | Walters et al. |
| 2002/0081748 A1 | 6/2002 | Roberts et al. |

FOREIGN PATENT DOCUMENTS

| | | |
|---|---|---|
| JP | 58-113760 A | 7/1983 |
| JP | 04-293249 | 10/1992 |
| JP | 06-174616 | 6/1994 |
| JP | 07-151714 | 6/1995 |
| JP | 2001-077158 | 3/2001 |
| JP | 2002-184828 | 6/2002 |
| JP | 2003-139666 | 5/2003 |

OTHER PUBLICATIONS

Vandenburg et al. "Analytical Extraction of Additives From Polymers", Analyst, 1997, v. 122, pp. 101R-115R.*

Vandenburg et al., "A simple solvent selection method for accelerated solvent extraction of additives from polymers", Analyst, 1999, v. 124, pp. 1707-1710.*

Gnanou and Fontanille, "Organic and Physical Chemistry of Polymers" (Williey and Sons, translation 2008, publication date 2002). pp. 478 and 479.*

Carrott et al., Identification and analysis of polymer additives using packed-column supercritical fluid chromatography with APCI mass spectrometric detection, Analyst, 1998, v. 123, pp. 1827-1833.*

Médard et al. "Characterization of additives at polymer surfaces by ToF-SIMS", Surface and Interface, Analysis, 2002, v. 34, pp. 565-569.*

Li et al. "Probing Aqueous Surfaces by TOF-SIMS", Chromatography Online, Oct. 1, 2011.*

"Separation and Analysis Technology of Polymer Additives", Technical Information Institute Co., Ltd pp. 19-21, Publication Date: Oct. 15, 1999.

European Patent Office; Office Action in European Patent Application No. 04 792 357.8 (Jan. 20, 2011).

Naka et al., *Development of Rapid Screening Method for Brominated Flame Retardants in Plastics by Time of Flight Secondary Ion Mass Spectrometry*, Proceedings of the ISWA World Environment Congress, Rome, Italy, (Oct. 17-21, 2004).

Naka et al., *Development of Rapid Screening Method for Brominated Flame Retardants and Hexavalent Chromium by Time-of-Flight Secondary Ion Mass Spectrometry (TOF-SIMS)*, vol. 48, No. 6, Shinku, pp. 365-371 (2005), published by The Vacuum Society of Japan.

Naka et al., *Rapid Screening Method for Brominated Flame Retardants and Hexavalent Chromium by Time-of-Flight Secondary Ion Mass Spectrometry (TOF-SIMS)*, Fourth Intl. Symposium on Environmentally Conscious Design and Inverse Manufacturing, Tokyo, Japan, pp. 818-822, (Dec. 12-14, 2005).

Kurokawa, title in Japanese, Clean Technology, pp. 29-32 (2005) with partial English language translation.

* cited by examiner

Brominated flame-retardant concentration (%)

METHOD OF DETERMINING MINUTE AMOUNTS OF ADDITIVES IN POLYMERS

TECHNICAL FIELD

The present invention relates to methods of analyzing minute content of materials, and, more specifically, relates to methods of analyzing minute quantities such as additives included in polymer materials.

BACKGROUND ART

A flowchart in FIG. 23 represents a conventional method of analyzing additives included in polyolefin-group resins, such as polypropylene (referred to as PP) and polyethylene (referred to as PE). First, the additives are extracted for 8 hours with a solvent, such as chloroform, heated to its boiling point, from pellets of the polyolefin-group resin, referred to as a sample (referred to as process "A"). Here, this extraction is performed twice, and thus, all of the additives are extracted. Next, after chloroform is removed from the additives, reflux extraction is performed for 1 hour using heated acetone (referred to as process "B"); then, after the acetone is removed, an analysis is performed by either liquid chromatography or gas chromatography. Consequently, the additives, such as an antioxidant and a flame retardant, are identified and quantified. On the other hand, regarding the residues remaining after the chloroform extraction, extraction is performed for 4 hours using heated N,N-dimethylformamide (referred to as process "C"); then, the extract obtained is analyzed by infrared spectroscopy, and thus, an additive such as a metal deactivator is identified.

In the process "A", an acetone/toluene solvent mixture, 1:1 by volume ratio, can also be used as the solvent instead of chloroform. As a method for the process "A", for example, the Soxhlet extraction method is used, in which the extraction is not limited to two times, but performed more than twice in response to necessity. Here, in the Soxhlet extraction method used for the process "A", because the extraction is performed with the solution being refluxed, a specified volume of the solution is needed; thus, as chloroform, for example, a volume of approximately 100 ml is needed. Therefore, the sample pellets weigh approximately 10 g. Additionally, in the process "A", because the extraction is performed using the solvent heated close to its boiling point, due to the resin of the base material being partially extracted, there is interference in the analysis; therefore, by re-extracting the additives from chloroform extract using acetone, which can only extract the additives, there is no interference in the analysis. Here, in the process "A", if a solvent that extracts only the additives is used, the extraction time is extended (for example, as referred to in Non-Patent Document 1).

[Non-Patent Document 1]
Technical Information Institute, Ed., "Separation and Analysis Technology of Polymer Additives", on page 19-21.

DISCLOSURE OF THE INVENTION

As described above, in the conventional method of analyzing a minute content of a material, although analyzing an extract has not required a long time because of using instrumental analysis. However, preparing the sample, because of a plural number of extraction treatments taking a long time and because a plurality of different methods are used a remarkably long time has been required; consequently, a problem has occurred in which the minute content cannot be rapidly identified and quantified.

An objective of the present invention, which is made to solve the above described problem, is to provide a method of rapidly analyzing a minute content included in a material, in which sample preparation, when the minute content included in the material is analyzed, is performed by one short-time extraction treatment without a plural number of the extraction treatments taking a long time and a plurality of different extraction-treatment methods.

According to a first aspect of the present invention, a method of analyzing a minute content by analyzing an extract extracted with a solvent from the material includes a step of mounting on a sample table a sample piece of the material to be analyzed; a step of dropping onto the sample table the solvent for extracting the content from the sample piece, and injecting the solvent into a gap between the sample table and the sample piece; a step of maintaining at room temperature the solvent injected into the gap between the sample table and the sample piece, and, with the solvent maintained in the gap between the sample table and the sample piece, extracting the content from the sample piece; and a step of analyzing the content extracted from the sample piece.

According to a second aspect of the present invention, a method of analyzing a minute content by analyzing an extract extracted with a solvent from a polymer material includes a step of mounting, in contact with the top face of a sample table, a sample piece of the polymer material to be analyzed; a step of dropping onto the sample table the solvent for extracting the content from the sample piece, and injecting the solvent into a gap between the top face of the sample table and the sample piece mounted in contact with the top face of the sample table; a step of maintaining at room temperature the solvent injected into the gap between the top face of the sample table and the sample piece, and, with the solvent maintained in the gap between the top face of the sample table and the sample piece, extracting the content from the sample piece; and a step of analyzing the content extracted from the sample piece.

According to a third aspect of the present invention, in the method of analyzing the minute content according to the second aspect, the step of analyzing the content extracted from the sample piece includes chromatographically analyzing the content extracted from the sample piece.

According to a fourth aspect of the present invention, in the method of analyzing the minute content according to the second aspect, the step of analyzing the content extracted from the sample piece includes, after removing, by vaporization, of the solvent from the content extracted from the sample piece so as to deposit the content onto the surface of a substrate used as the sample table, analyzing the content deposited on the surface of the substrate.

According to a fifth aspect of the present invention, the method of analyzing the minute content according to the fourth aspect, the method of analyzing the content deposited on the surface of the substrate is time-of-flight secondary ion mass spectrometry.

According to a sixth aspect of the present invention, in the method of analyzing the minute content according to the second aspect, the step of extracting the content from the sample piece includes vibrating the substrate while the solvent is maintained at room temperature in the gap between the top face of the sample table and the sample piece, and the solvent is maintained in the gap between the top face of the sample table and the sample piece.

According to a seventh aspect of the present invention, in the method of analyzing the minute content according to the second aspect, the step of extracting the content from the sample piece includes maintaining the solvent in the gap between the top face of the sample table and the sample piece in a saturated vapor atmosphere, at room temperature, while the solvent is maintained in the gap between the top face of the sample table and the sample piece.

According to an eighth aspect of the present invention, in the method of analyzing the minute content according to the fifth aspect, the solvent, maintained in the gap between the top face of the sample table and the sample piece, for extracting the content from the sample piece includes a silver composition dissolved in the solvent.

According to the first aspect of the present invention, the method of analyzing the minute content by analyzing the extract extracted with the solvent from the material includes the step of mounting on the sample table the sample piece of the material to be analyzed; the step of dropping onto the sample table the solvent for extracting the content from the sample piece, and injecting the solvent into the gap between the sample table and the sample piece; the step of maintaining at room temperature the solvent injected into the gap between the sample table and the sample piece, and, with the solvent maintained in the gap between the sample table and the sample piece, extracting the content from the sample piece; and the step of analyzing the content extracted from the sample piece, whereby, the extraction time can be shortened, and, using a small sample piece, accurate analysis of the content in the material can be performed in a short time.

According to the second aspect of the present invention, the method of analyzing the minute content by analyzing the extract extracted with the solvent from the polymer material includes the step of mounting, in contact with the top face of the sample table, the sample piece of the polymer material to be analyzed; the step of dropping onto the sample table the solvent for extracting the content from the sample piece, and injecting the solvent into the gap between the top face of the sample table and the sample piece mounted in contact with the top face of the sample table; the step of maintaining at room temperature the solvent injected into the gap between the top face of the sample table and the sample piece, and, with the solvent maintained in the gap between the top face of the sample table and the sample piece, extracting the content from the sample piece; and the step of analyzing the content extracted from the sample piece, whereby, the extraction time can be shortened, and, using a small sample piece, accurate analysis of the content in a polymer material can be performed in a short time.

According to the third aspect of the present invention, in the method of analyzing the minute content according to the second aspect, the step of analyzing the content extracted from the sample piece includes chromatographically analyzing the solution including the content extracted from the sample piece, whereby the extraction time can be shortened and, using a small sample piece, accurate analysis of the content in a polymer material can be performed in a short time.

According to the fourth aspect of the present invention, in the method of analyzing the minute content according to the second aspect, the step of analyzing the content extracted from the sample piece includes, after removing, by vaporization of the solvent in the solution including the content extracted from the sample piece so as to deposit the content onto the surface of the substrate used as the sample table, analyzing the content deposited on the surface of the substrate, whereby the extraction time can be shortened, and, using a small sample piece, accurate analysis of the content in the polymer material can be performed in a short time.

According to the fifth aspect of the present invention, the method of analyzing the minute content according to the fourth aspect, the method of analyzing the content deposited on the surface of the substrate is time-of-flight secondary ion mass spectrometry, whereby the extraction time can be shortened, and, using a small sample piece, accurate analysis of the content in a polymer material can be performed in a short time. Especially, analysis of a minute content becomes possible.

According to the sixth aspect of the present invention, in the method of analyzing the minute content according to the second aspect, as the step of extracting the content from the sample piece, the method of extracting includes vibrating, the sample table while the solvent is maintained at room temperature in the gap between the top face of the sample table and the sample piece, using the solvent maintained in the gap between the top face of the sample table and the sample piece, whereby, the extraction time can be shortened, and a small amount of the sample piece is used, so that accurate analysis of the content in a polymer material can be performed in a short time. Especially, because the amount of the extract from the sample piece is increased, the analysis accuracy of the extract is improved.

According to the seventh aspect of the present invention, in the method of analyzing the minute content according to the second aspect, as the step of extracting the content from the sample piece, the method of extracting includes maintaining the solvent in the gap between the top face of the sample table and the sample piece in a saturated vapor atmosphere, at room temperature, and extracting the content from the sample piece, whereby, the extraction time can be shortened, and, a small sample piece is used, and accurate analysis of the content in a polymer material can be performed in a short time. Especially, because the re-dropping of the solvent used for the extraction becomes unnecessary, the analysis process becomes simple.

According to the eighth aspect of the present invention, in the method of analyzing the minute content according to the fifth aspect, the solvent, maintained in the gap between the top face of the sample table and the sample piece, for extracting the content from the sample piece additionally includes a silver composition dissolved in the solvent, whereby, the extraction time can be shortened, and, using a small sample piece, accurate analysis of the content in a polymer material can be performed in a short time. Especially, the sensitivity, using time-of-flight secondary ion mass spectrometry for analyzing the extract from the material, is remarkably improved.

BEST MODE FOR CARRYING OUT THE INVENTION

Figure 1:
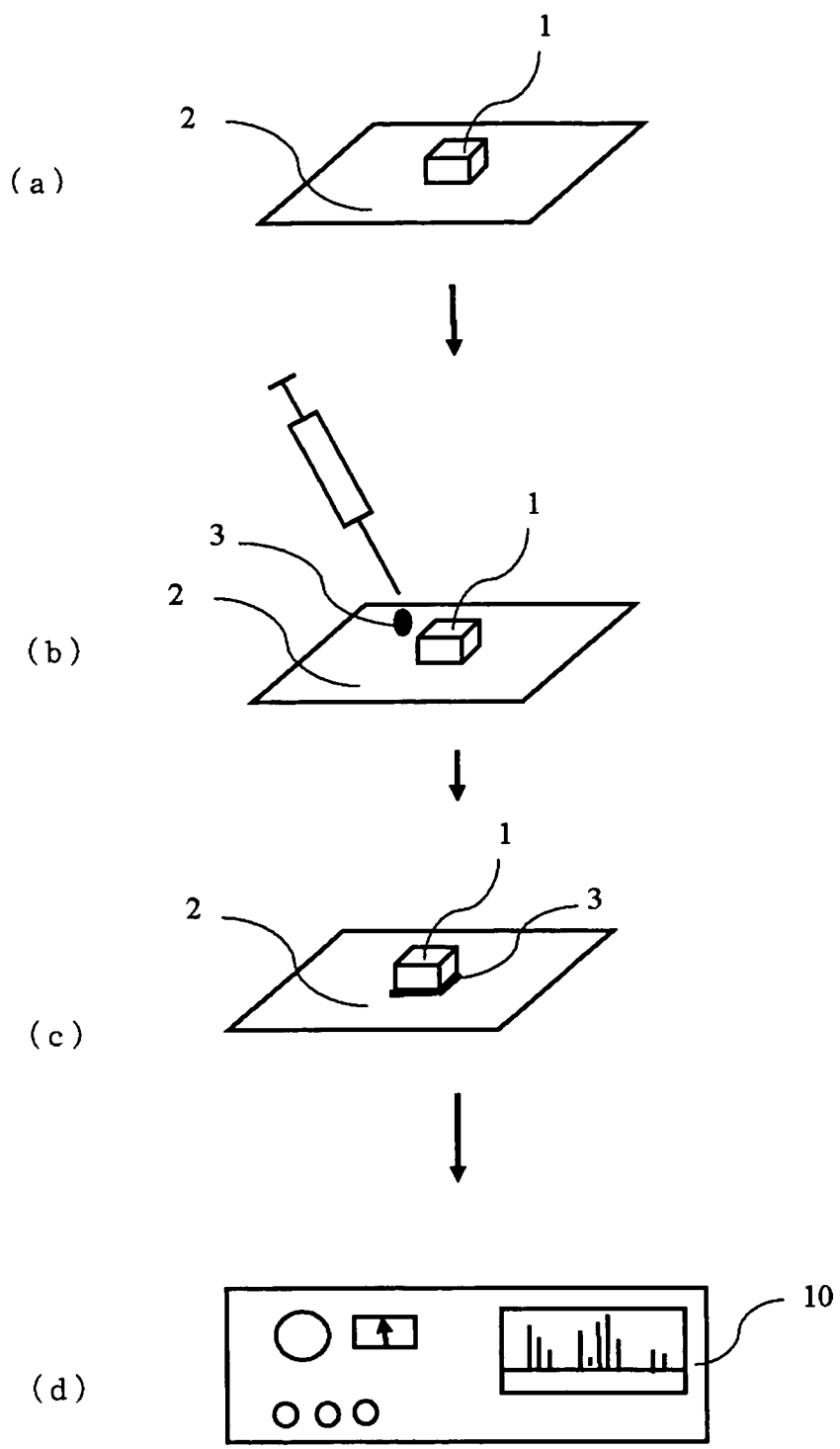
FIG. 1 is a flow chart explaining a method of analyzing a minute content included in a material according to the present invention.

FIG. 1 is a flow chart explaining a method of analyzing a minute content included in a material according to the present invention. In a first step, a sample piece 1 of the material including a substance to be analyzed is mounted in contact with the top face of a sample table 2 (FIG. 1(a)). In a second step, a solvent 3 for extracting the content from the sample piece 1 is dropped onto the top face of the sample table 2 the solvent enters gaps between the top face of the sample table 2 and the sample piece 1 (hereinafter referred to as "gaps between the sample table 2 and the sample piece 1") (FIG. 1(b)). In a third step, the solvent 3 in the gaps between the sample table 2 and the sample piece 1 is kept for a short time at room temperature; thus, by maintaining the solvent 3 in the gaps between the sample table 2 and the sample piece 1, the content to be analyzed is extracted from the sample piece 1 (FIG. 1(c)). In a fourth step, the content extracted from the sample piece 1 is analyzed by an instrumental analyzer 10 (FIG. 1(d)).

In the analyzing method according to the present invention, as the material to be analyzed, polymer materials such as plastics, rubber, adhesives, encapsulating resin, and molding resin are listed. These polymer materials are analyzed not only in the state of the materials themselves, but also in a state in which the materials are used in instrumental parts, such as a molded product, and a printed wiring board. In the analyzing method according to the present invention, as materials to be analyzed, a sub-material such as an antioxidant, a fire retardant, a curing catalyst, or a processing aid included in a polymer material, in a minute content, may be added either during production of the material itself, or when the material is being molded/processed into various parts of a product; however, if the substance that can be extracted with a solvent from the polymer material is used, the material is not limited to the above. In the analyzing method according to the present invention, a small sample piece, such as one resin pellet, for example, 0.1-0.5 g in weight, may also be used.

In the analyzing method according to the present invention, as the sample table for mounting the sample piece, any table having a flat face that can support the sample piece may be applied, and, especially, a substrate is preferably applied. As the materials of the sample table, a glass material, an inorganic material, a metallic material, and a plastic material having chemical resistance, etc., that does not include the substance to be analyzed, is used. When liquid chromatography, gas chromatography, or liquid chromatography/mass spectrometry is applied as the analyzing method, specifically, for example, a glass substrate, a silicon substrate, a germanium substrate, a silver substrate, a gold substrate, a poly(tetrafluoroethylene) substrate, an SUS substrate coated with poly(tetrafluoroethylene), a glass Petri dish, a silver container, a gold container, or a poly(tetrafluoroethylene) container, is used as the table. When infrared spectrum analysis is applied as the analyzing method, specifically, for example, a silicon substrate, a germanium substrate, or an SUS substrate coated with poly(tetrafluoroethylene) is used. Moreover, when the X-ray photoelectron spectroscopy method is applied as the analyzing method, a silicon substrate is used.

Furthermore, when time-of-flight secondary ion mass spectrometry is applied as the analyzing method, for example, a silicon substrate, a germanium substrate, a silver substrate, a gold substrate, or an SUS, substrate plated with silver or gold is used.

Figure 2:
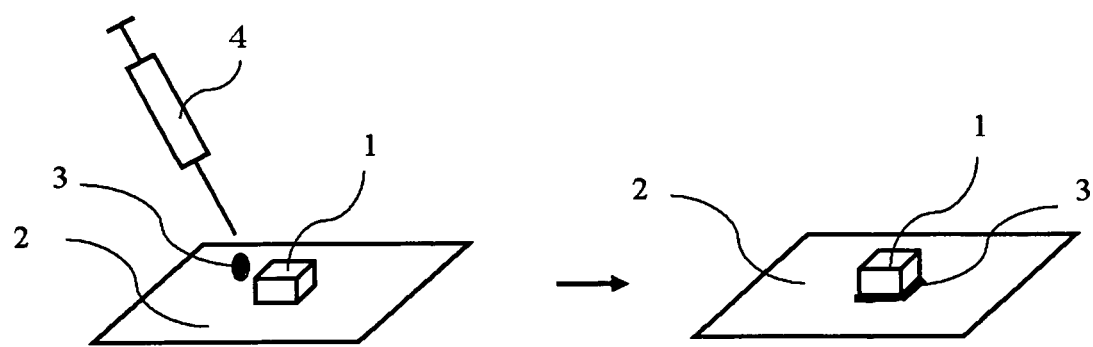
FIG. 2 illustrates states in which an extraction solvent is dropped, according to the analyzing method of the present invention.

FIG. 2 illustrates states in which the extraction solvent is dropped, according to the analyzing method of the present invention. As represented in FIG. 2, the extraction solvent 3 is dropped using a microsyringe 4 onto the top face of the sample table 2 on which the pellet of the sample piece 1 is mounted in contact with the table. In FIG. 2, a substrate as the sample table 2 is represented as an example; hereinafter, a substrate 2 is explained as the sample table 2. However, according to the present invention, the sample table 2 is not limited to the substrates mentioned. Regarding the dropping volume of the extraction solvent 3, the volume may be from a volume that can at least fill the gaps between the substrate 2 and the sample piece 1 to a volume that is twice the volume of the sample piece; thereby, for example, when the sample piece 1 is a single resin pellet, the volume is 5-100 µl. Moreover, if the position where the solvent is to be dropped is on the top face of the substrate 2, the position is not especially limited; however, it is preferable to drop the solvent at a position, on the top face of the substrate 2, close to a portion on which the sample piece 1 is mounted, specifically, to drop at the boundary between the portion on which the sample piece 1 is mounted and the portion on which the sample piece 1 is not mounted, because the solvent 3 can be effectively injected, i.e., drawn, into the gaps between the substrate 2 and the sample piece 1.

Figure 3:
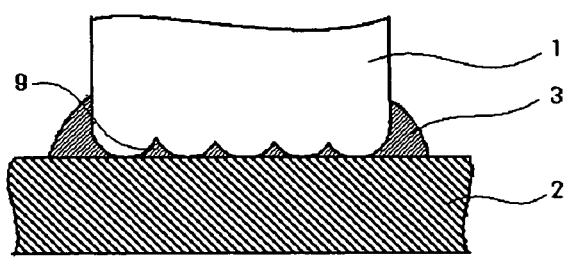
FIG. 3 is a view illustrating a state, according to the analyzing method of the present invention, in which a sample piece is mounted in contact with the top face of a sample table, and the extraction solvent is maintained in gaps between the top face of the sample table and the sample piece.

FIG. 3 is a view illustrating a state in which the sample piece 1 is mounted in contact with the top face of the substrate as the sample table 2. As represented in FIG. 3, the sample piece 1 has recesses and protrusions on its face contacting the substrate 2; thereby, these protrusions contact the top face of the substrate 2, meanwhile the recesses form gaps 9 between the substrate 2 and the sample piece 2, and, thus, the solvent dropped is drawn into the gaps 9 by capillary action. In the extraction of the content from the sample piece 1 according to the analyzing method of the present invention, the solvent 3 maintained in the gaps 9 between the substrate 2 and the sample piece 1 is held at room temperature for a short time; thereby, the content is extracted into the solvent 3 contacting the sample piece, especially into the solvent 3 in the gaps between the substrate 2 and the sample piece 1. At this time, because the solvent decreases due to vaporization, after a predetermined time passes, additional solvent 3 may be dropped. For example, if the sample piece 1 is a single resin pellet, the extraction time, that is, the time during which the solvent 3 is maintained in the gaps between the substrate 2 and the sample piece 1, and the content being extracted is preferably set for 0.5-30 minutes, and further preferably set for 0.5-15 minutes. If this time is shorter than 0.5 minutes, the extraction is insufficient; thereby, the analysis accuracy deteriorates. On the other hand, if the time is longer than 30 minutes, the number of times of the dropping the solvent increases without an increase in the extracted content; thereby, not only the analysis process becomes more complex, but also the analysis time becomes longer.

Moreover, in order to increase the amount of the content extracted from the sample piece 1 into the solvent 3, the substrate 2 may be vibrated during the extraction. As the vibration source, an ultrasonic washer or a shaker may be used, an ultrasonic oscillator may be pasted onto the substrate 2. Furthermore, by putting the substrate 2 and the sample piece 1 into a sealed container, and maintaining the solvent 3 in the gaps between the substrate 2 and the sample piece 1, the extraction of the content may be performed from the sample piece 1 using the extraction solvent 3, in a saturated vapor atmosphere of the same solvent as the extraction solvent 3. According to this operation, loss of the extraction solvent 3 due to vaporization is prevented, and additional dropping of the solvent is not necessary; consequently, the analyzing process can be simplified.

Figure 4:
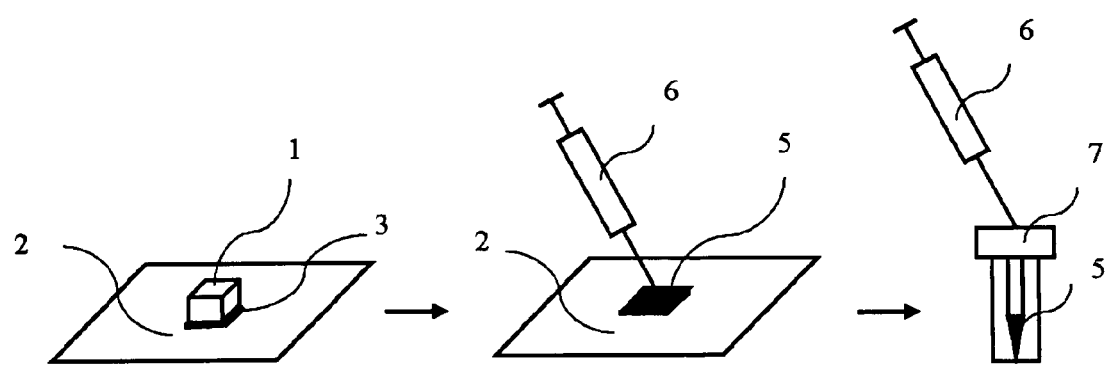
FIG. 4 represents a first method of preparing a specimen for analyzing an extract, according to an analyzing method of the present invention.

FIG. 4 represents a first method of preparing a specimen for analyzing the extract using an analyzer, according to an analyzing method of the present invention. This first method is especially used when the extract is analyzed by liquid chromatography, gas chromatography, or liquid chromatography/mass spectrometry. As represented in FIG. 4, after the extraction step has finished, the sample piece 1 is removed from the substrate 2; then, solution 5 including the extract on the top face of the substrate 2 is sampled using a microsyringe 6 and placed into a sample cell 7. Then, this sampled solution 5 is injected into the analyzer, and the content included in the polymer material is analyzed.

Figure 5:
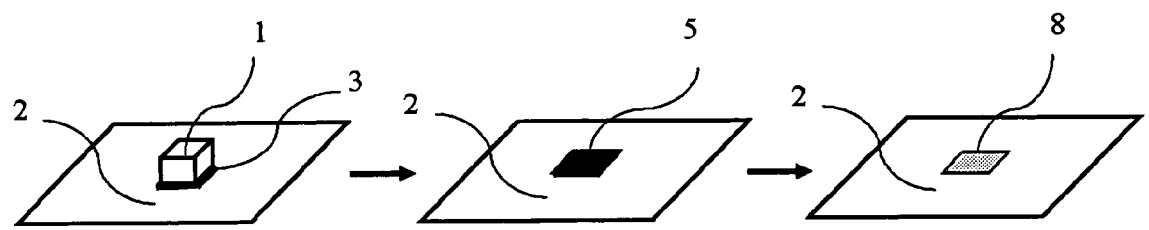
FIG. 5 illustrates a second method of preparing a specimen for analyzing an extract, according to an analyzing method of the present invention.

FIG. 5 illustrates a second method of preparing a specimen for analyzing the extract using an analyzer, according to an analyzing method of the present invention. This second method is used when the extract is analyzed by any one of X-ray fluorescence spectrometry, time-of-flight secondary ion mass spectrometry, infrared spectrometry, and X-ray photoelectron spectroscopy. As represented in FIG. 5, after the extraction step has finished, the sample piece 1 is removed from the substrate 2, and then the solvent of the solution 5 including the extract on the top face of the substrate 2 is removed by vaporization; thus, the substrate surface on which extract 8 is deposited is directly analyzed by the analyzer. In the analyzing method of the present invention, especially, when the extract is analyzed using time-of-flight secondary ion mass spectrometry, if too much extract is present, the deposition portion is charged; therefore, in order to prevent the charging, it is preferable that a silver substrate, a gold substrate, or an SUS substrate on which silver or gold is plated is used as the substrate. In the analyzing method of the present invention, as the solvent used for extracting, a solvent is used that extracts the content without decomposing the polymer material at room temperature. Regarding the grade of the solvent used, a solvent having the analysis grade purity is preferably used because of little influence on analyzing the content.

In the analyzing method of the present invention, especially, when the extract is analyzed using time-of-flight secondary ion mass spectrometry, the content is dissolved in a solvent for extraction, and, if the solution used, including a silver compound that does not include as an impurity the substance to be measured, not only the charging can be prevented, even if a chargeable substrate is used, but also the analysis sensitivity is improved; consequently, the analysis accuracy is improved. In the analyzing method of the present invention, the sample piece is mounted in contact with the top face of the sample table, such as a substrate, the solvent is inserted, by dropping into the gaps between the sample table and the sample piece, the solvent is maintained in the gaps between the sample table and the sample piece, the content is extracted with this solvent, and the extract is analyzed using an analyzer; therefore, the extraction time can be shortened, and, using a small sample piece, accurate analysis of the content in the material, especially in a polymer material, can be performed in a short time. Hereinafter, more specific examples according to the present invention are presented; however, the present invention is not limited to these examples.

EXAMPLES

Example 1

High density polyethylene (hereinafter referred to as HDPE) specimens including an antioxidant in a concentration of 50 ppm, 100 ppm, and 1000 ppm by weight were prepared. HJ340™ (produced by Japan Polychem Corp.) was used as HDPE, and 1,3,5-trimethyl-2,4,6 tris(3,5-di-tert-butyl-4-hydroxybenzyl)benzene (Irganox 1330™, produced by Aldrich Corp.) was used as the antioxidant. As the sample piece 1, the antioxidant was added to and kneaded with the HDPE so that the concentrations listed above were prepared; thus, pellets were prepared in which the size of a single pellet is 5 mm×3 mm×3 mm, and the weight is approximately 0.2 g. Similarly to the method represented in FIG. 2, a single HDPE pellet as the sample piece 1 was mounted in contact with a silicon substrate as the sample table 2, and 20 µl of chloroform as the extraction solvent 3 was dropped using the microsyringe 4 so that the chloroform was inserted into the gaps between the HDPE pellet and the silicon substrate. Chloroform is a solvent that does not dissolve HDPE, but dissolves the antioxidant. The sample was kept at room temperature for 10 minutes after the dropping operation; however, because the volume of the chloroform decreases due to vaporization, 20 µl chloroform was additionally dropped every two minutes. The chloroform used was liquid chromatography grade (produced by Wako Pure Chemical Industries, Ltd.).

Similarly to the method represented in FIG. 4, after 10 minutes, the HDPE pellet as the sample piece 1 was removed from the silicon substrate as the sample table 2. Next, the chloroform solution as the solution 5 including an extract remaining on the top face of the silicon substrate was transferred into the sample cell 7 using the microsyringe 6, and then, adjusted to a constant volume of 50 µl. The time required from the start to this stage was 12 minutes. The solution in this sample cell 7 was injected into a liquid chromatography/mass spectrometry analyzer, and thus, the amount of the antioxidant was measured. Model HP8900™ (manufactured by Agilent Technologies Inc.) was used as the liquid chromatography analyzer, Model LC-mate™ (manufactured by JEOL Ltd.) was used as the mass spectrometry analyzer, and Inertsil ODS-3™ (manufactured by GL Sciences Inc.) having a column inner diameter of 4.6 mm and a length of 150 mm was used as a column for separating organic compounds. Regarding the measurement conditions of the liquid chromatography, the gradient mode using methanol and water as the eluent was applied, and the flow rate was set at 1 ml/minute. Regarding the measurement conditions of the mass spectrometry, the atmospheric pressure chemical ionization method was used as an ionization method, the positive ion mode was used, and the mass-to-charge ratio (referred to as "m/z") that is the ratio of the fragment mass number "m" to the charge "z" was set to 1-1000 as the measurement range; thus, the scanning measurement was performed.

Figure 6:
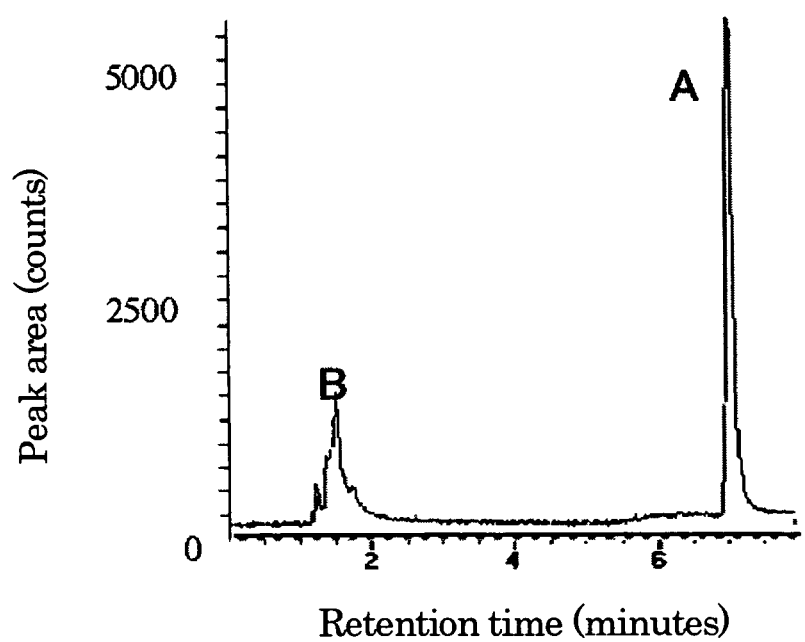
FIG. 6 is an example of the measurement results according to Example 1, and is a chromatogram of an extraction solution extracted from an HDPE pellet including an antioxidant in a concentration of 500 ppm.
Figure 7:
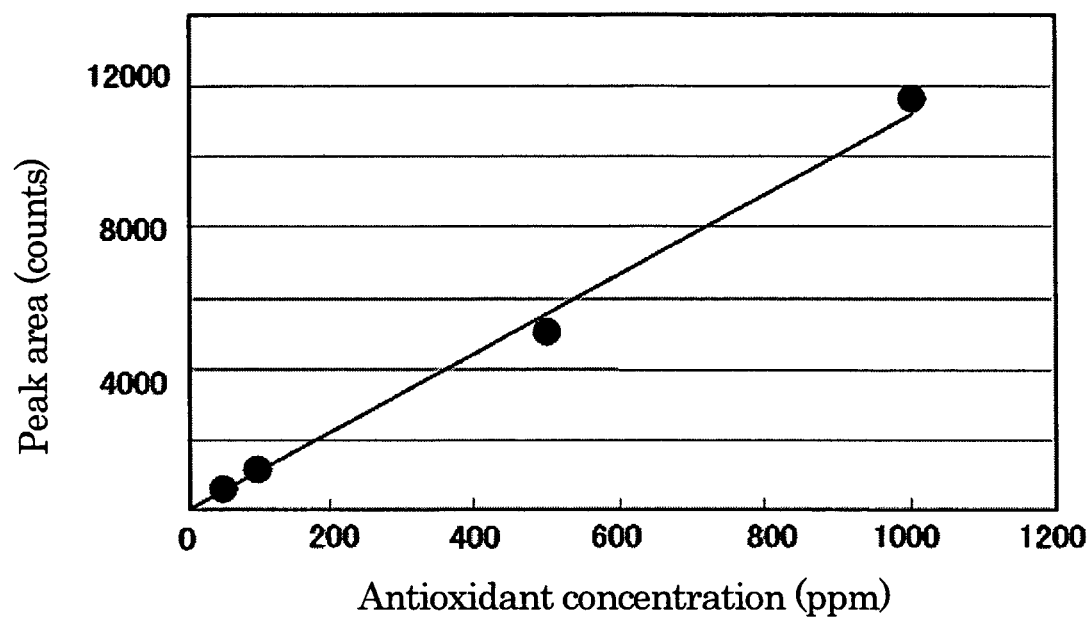
FIG. 7 is a graph representing a relationship between areas of the peaks "A" obtained from the chromatograms in which the extraction solutions extracted from HDPE pellets including an antioxidant in concentrations of 50 ppm, 100 ppm, 500 ppm, and 1000 ppm, respectively, according to Example 1.

FIG. 6 is, as an example of the measurement results, a chromatogram of the extraction solution extracted from the HDPE pellet including the antioxidant concentration of 500 ppm. The peak "A" represents the separated peak of the antioxidant, while the peak "B" represents a silane coupling agent included in the pellet. Identification of these peaks was confirmed by checking the mass spectrum and the retention times of the chromatogram based on the measurement of a standard sample using corresponding substances. The peak area of the peak "A" was 5000 counts. FIG. 7 is a graph representing a relationship between areas of the peaks "A" obtained from the chromatograms in which the extraction solutions extracted from the HDPE pellets including the antioxidant in concentrations of 50 ppm, 100 ppm, 500 ppm, and 1000 ppm. An excellent linear relationship was obtained between the antioxidant concentrations and the areas of the peaks "A" obtained from the chromatograms. In this example, the processing time was 12 minutes for extracting the antioxidant as the content from the HDPE pellet; thereby, it was found that the quantitative analysis of the antioxidant as the content can be performed by a short-time extraction treatment. As described above, in the analyzing method according to this example, the extraction processing time can be considerably shortened compared to that in the conventional method, and the antioxidant as the content included in the HDPE specimen can be rapidly analyzed.

Example 2

PP specimens including, as an additive, a brominated flame retardant in concentrations of 0.1%, 1%, and 10% by weight were prepared as samples. PC03B™ (produced by Japan Polychem Corp.) was used as PP, and decabromodiphenylether (produced by Wako Pure Chemical Industries, Ltd.) was used as the brominated flame retardant. As the sample piece 1, the brominated flame retardant was added to and kneaded with the PP so that the concentrations above were produced; thus, pellets were prepared in which a size of the single pellet is 5 mm×3 mm×3 mm, and the weight is approximately 0.2 g. Similarly to the method represented in FIG. 2, a single PP pellet as the sample piece 1 was mounted in contact with an SUS substrate coated with fluororesin as the sample table 2, and 20 µl toluene as the extraction solvent 3 was dropped using the microsyringe 4 so that the toluene is inserted into the gaps between the PP pellet and the SUS substrate coated with fluororesin. Toluene is a solvent that does not dissolve PP, but dissolves the brominated flame retardant. The sample was kept at room temperature for 10 minutes after the dropping operation; however, because the volume of the toluene decreases due to the vaporization, 20 µl toluene was additionally dropped after five minutes. The toluene used was liquid chromatography grade (produced by Wako Pure Chemical Industries, Ltd.). Because after 10 minutes from the first toluene drop, the dropped toluene had been removed by vaporization, the PP pellet and the substrate were in a dry state. Then, when the PP pellet was removed from the substrate, similarly to the case represented in FIG. 5, extract from the pellet was deposited on the surface of the substrate as a condensed substance.

Figure 8:
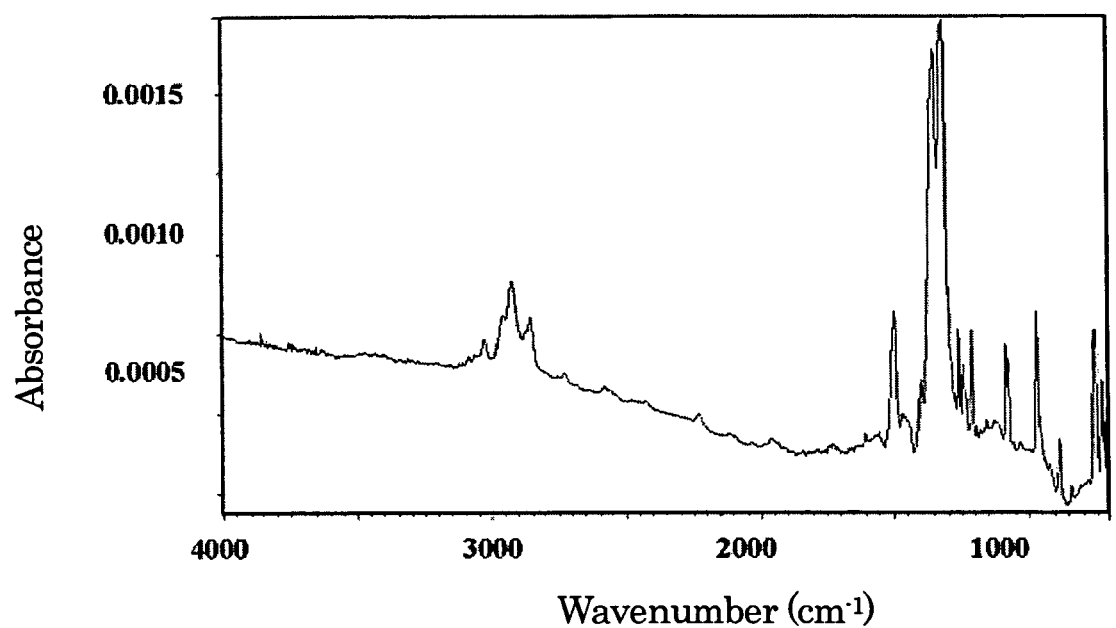
FIG. 8 is an example of the measurement results according to Example 2 and is an infrared absorption spectrum of an extract from a PP pellet including a brominated flame retardant in a concentration of 0.1%.
Figure 9:
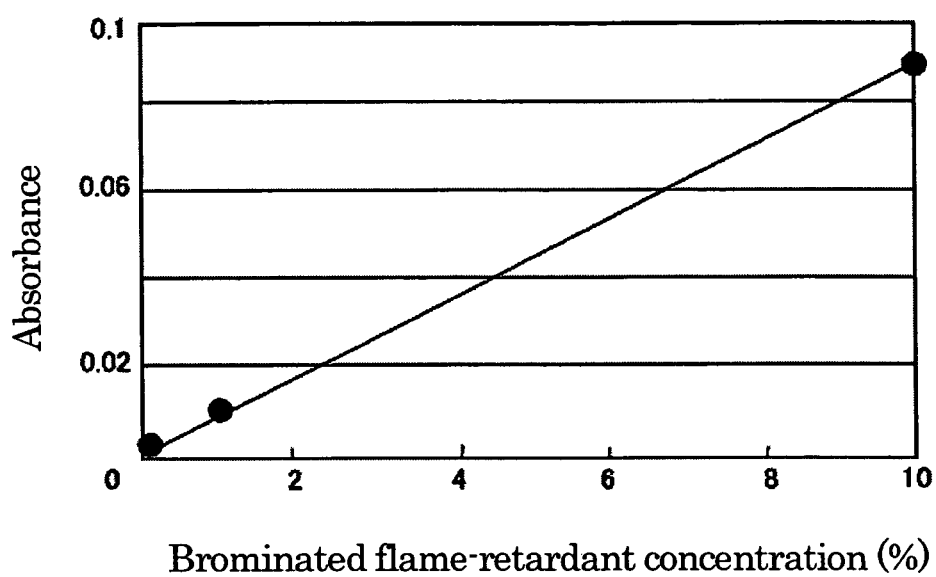
FIG. 9 is a graph representing a relationship between the absorbance values of the infrared absorption peaks obtained from the analysis in which extracts from PP pellets including a brominated flame retardant in a concentration of 0.1%, 1%, and 10%, respectively, according to Example 2.

This deposited substance on the surface of the substrate was analyzed by microscopic Fourier-transform infrared spectroscopy. Model JIR-5500™ (manufactured by JEOL Ltd.) was used as the microscopic Fourier-transform infrared spectrometer. Regarding the measurement conditions, the reflection mode was used, in which the measurement wavenumber range was set to 700-4000 $cm^{-1}$, and the wavenumber resolution was set at 2 $cm^{-1}$. FIG. 8 is, as an example of the measurement results, an infrared absorption spectrum of the extract extracted from the PP pellet including a brominated flame retardant concentration of 0.1%. As represented in FIG. 8, the infrared absorption peak caused by decabromodiphenylether was observed close to 1300 $cm^{-1}$. FIG. 9 is a graph representing a relationship between the absorbance values of the infrared absorption peaks obtained from the analysis in which the extract is extracted from PP pellets including the brominated flame retardant in concentrations of 0.1%, 1%, and 10%. An excellent linear relationship was obtained between the brominated flame-retardant concentrations and the absorbance values of the infrared absorption peaks. In this example, the processing time was 10 minutes for extracting the brominated flame retardant as the content from the PP pellet; thereby, it was found that the quantitative analysis of the brominated flame retardant as the content can be performed by short-time extraction treatment. As described above, in the analyzing method according to this example, the extraction processing time can be considerably shortened compared to that in the conventional method, and the brominated flame retardant as the content included in the PP specimen can be rapidly analyzed.

Example 3

Figure 10:
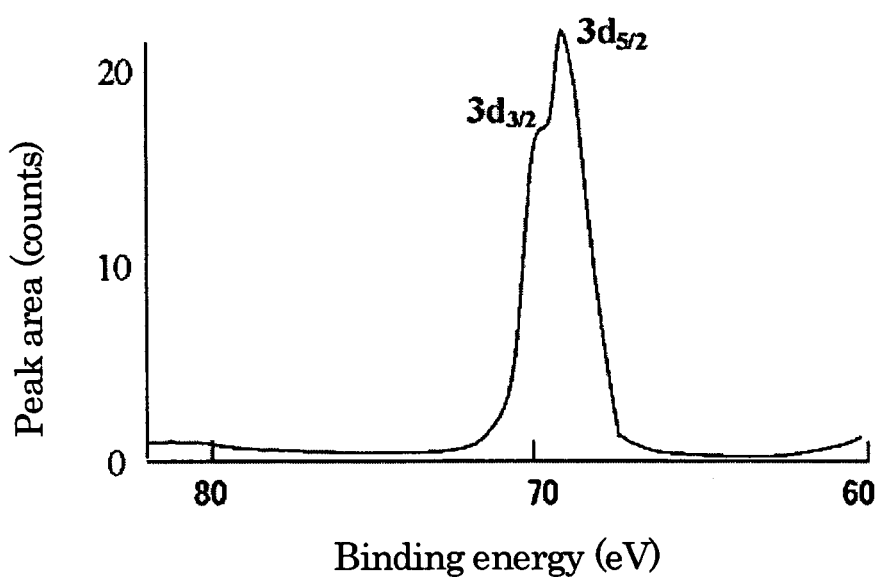
FIG. 10 is, as an example of the measurement results according to Example 3, a photoelectron spectrum of an extract from a PP pellet including a brominated flame retardant in a concentration of 0.1%.
Figure 11:
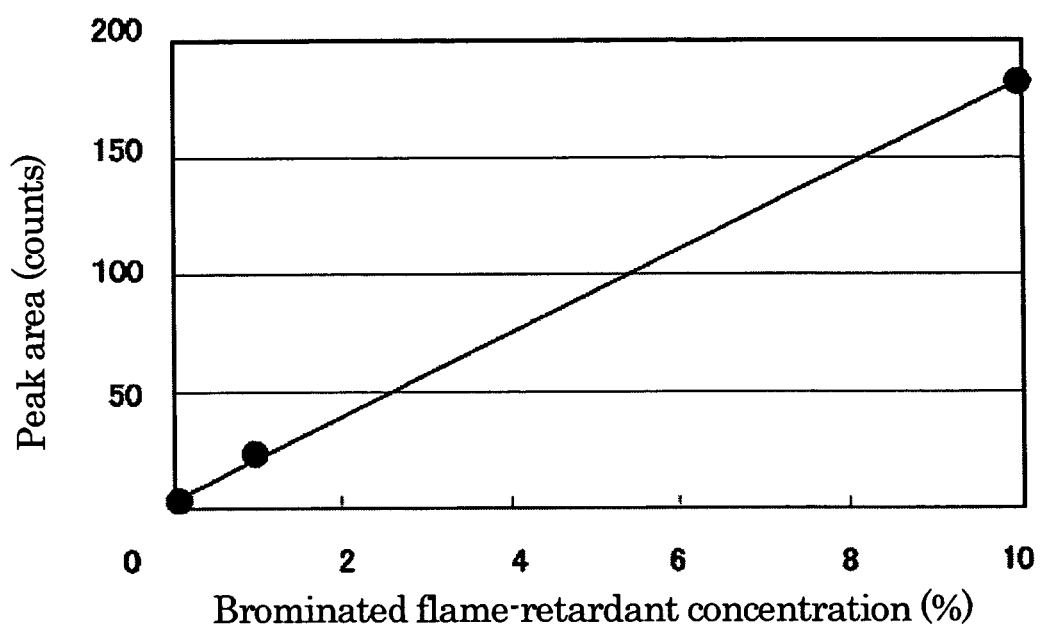
FIG. 11 is a graph representing a relationship between peak areas at close to 69 eV of photoelectron spectra obtained from the analysis of extracts from PP pellets including a brominated flame retardant in concentrations of 0.1%, 1%, and 10%, respectively, according to Example 3.

Except for a silicon substrate being used as the substrate to be the sample table 2, the drop operation using the extraction solvent, the extraction operation, and the deposition/fixation operation of the extract were performed similarly to the procedure in Example 2. In this example, the deposited substance on the surface of the substrate was analyzed by X-ray photoelectron spectroscopy. Model QUANTUM2000™ (manufactured by Physical Electronics Industries Inc.) was used as the X-ray photoelectron spectroscopic analyzer, and the measurement range was set to 60-80 eV. FIG. 10 is, as an example of the measurement results, a photoelectron spectrum of the extract extracted from the PP pellet including the brominated flame retardant in a concentration of 0.1%. As represented in FIG. 10, the photoelectron spectrum caused by the $3d_{3/2}$ and $3d_{5/2}$ orbits of bromine included in decabromodiphenylether was observed close to 69 eV, and the spectrum peak area was 20. FIG. 11 is a graph representing a relationship between the peak areas at 69 eV of the photoelectron spectra obtained from the analysis in which the extract is extracted from the PP pellets including the brominated flame retardant in concentrations of 0.1%, 1%, and 10%. An excellent linear relationship was obtained between the brominated flame-retardant concentrations and the peak area. In this example, the processing time was 10 minutes for extracting the brominated flame retardant as the content from the PP pellet; thereby, it was also found that the quantitative analysis of the brominated flame retardant as the content can be performed by a short-time extraction operation. As described above, in the analyzing method according to this example, the extraction processing time can also be considerably shortened compared to that in the conventional method, and the brominated flame retardant as the content included in the PP specimen can be rapidly analyzed.

Example 4

Except for HDPE pellets including the antioxidant in concentrations of 10 ppm, 50 ppm, 100 ppm, 500 ppm, or 1000 ppm by weight being prepared as the sample pieces 1, similarly to the procedure in Example 1, the drop operation using the extraction solvent, and the extraction operation were performed. In this example, after ten minutes passed from the first dropping of chloroform, the HDPE pellet was removed from the top face of the substrate without dropping chloroform again. Next, the substrate was kept for two minutes at room temperature so that the chloroform was removed by vaporization; thus, extract from the pellet was deposited as a condensed substance on the surface of the substrate. In this example, the deposited substance on the surface of the substrate was analyzed by time-of-flight secondary ion mass spectrometry. TRIFT2™ (manufactured by ULVAC-PHI Inc.) was used as the time-of-flight secondary ion mass spectrometer analyzer. Regarding the measurement conditions, $^{69}Ga^+$ ion was used as the primary ion, the measurement mode of the secondary ion was set to the positive ion mode, the measurement range was set to m/z=1-1000, and the mass resolution was set to approximately ΔM/M=5000.

Figure 12:
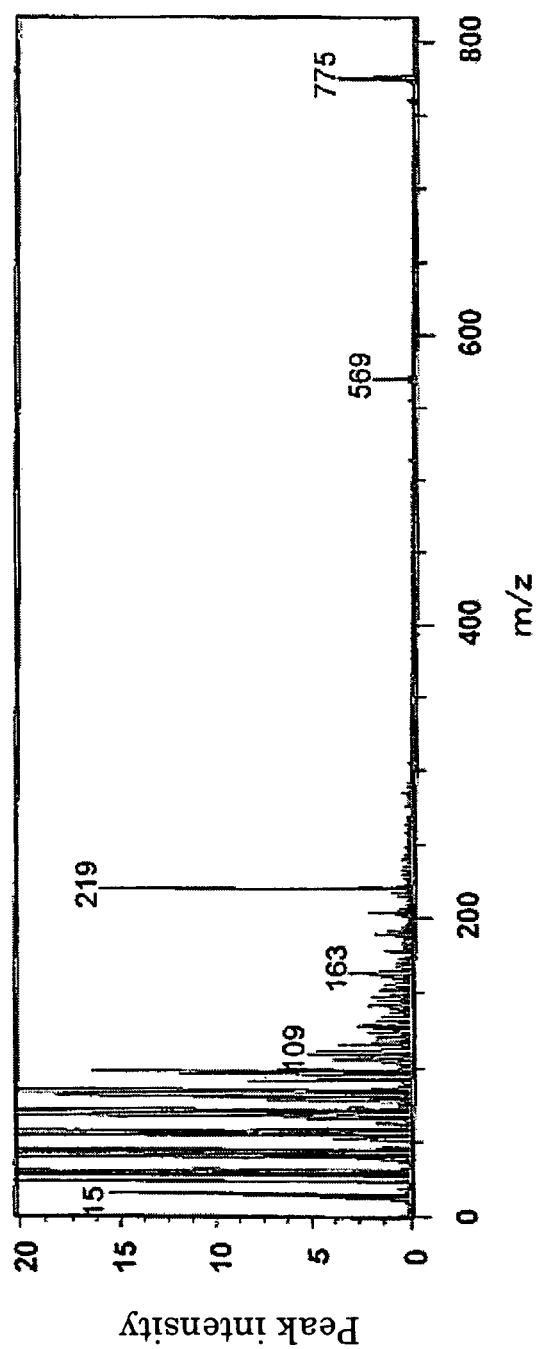
FIG. 12 is, as an example of the measurement results according to Example 4, a mass spectrum of an extract from an HDPE pellet including an antioxidant in a concentration of 500 μm.
Figure 13:
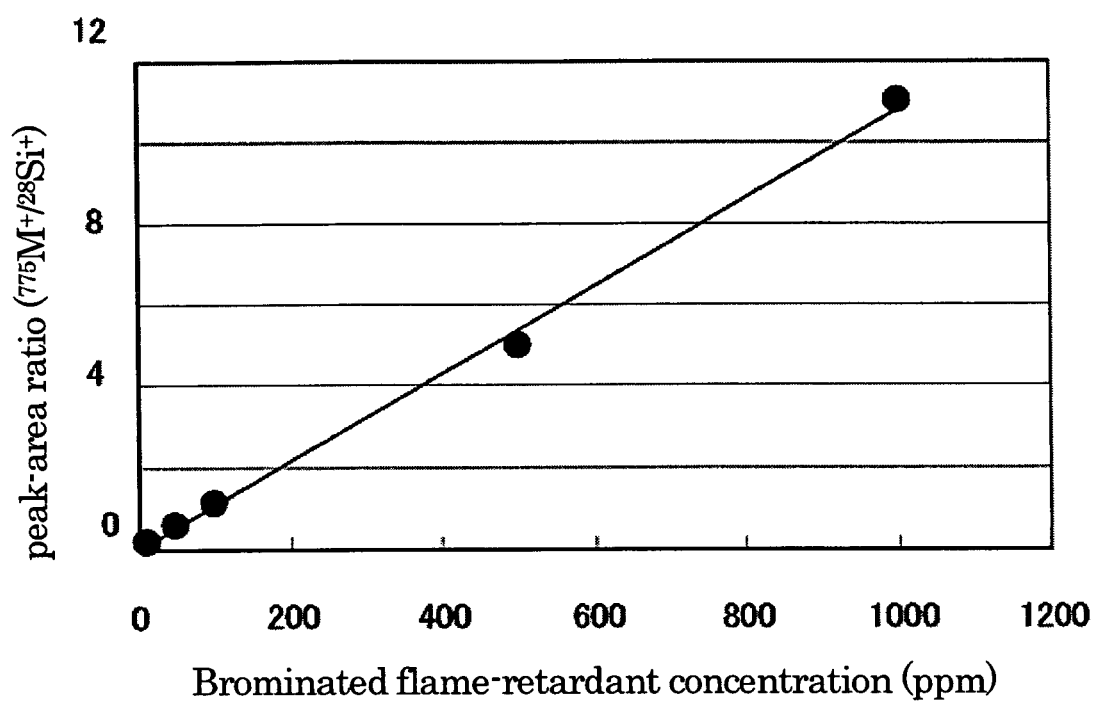
FIG. 13 is a graph representing a relationship between the mass-spectrum peak-area ratios ($^{775}M^+/^{28}Si^+$) obtained from an analysis of extracts from HDPE pellets including an antioxidant in concentrations of 10 ppm, 50 ppm, 100 ppm, 500 ppm, and 1000 ppm, respectively, according to Example 4.

FIG. 12 is, as an example of the measurement results, a mass spectrum of the extract extracted from the HDPE pellet including the antioxidant in a concentration of 500 ppm. As represented in FIG. 12, the mass peak caused by the fragment of the antioxidant was observed at m/z=775. Quantitative analysis was performed using the normalized ($^{775}M^+/^{28}Si^+$) area ratio in which the area of the peak at m/z=775 ($^{775}M^+$) is normalized by the area of the peak at m/z=28 ($^{28}Si^+$) caused by the silicon included in the substrate. The area ratio of the extract extracted from the HDPE pellet including the antioxidant in a concentration of 500 ppm was 5. FIG. 13 is a graph representing a relationship between the mass spectrum peak area ratios ($^{775}M^+/^{28}Si^+$) obtained from the analysis of the extracts extracted from the HDPE pellets including the antioxidant in concentrations of 10 ppm, 50 ppm, 100 ppm, 500 ppm, and 1000 ppm. An excellent linear relationship was obtained between the antioxidant concentrations and the peak-area ratios ($^{775}M^+/^{28}Si^+$), and especially, it was found to be also detectable at a concentration of 10 ppm. In this example, the processing time was 12 minutes for extracting the antioxidant as the content from the HDPE pellet; thereby, it was found that the quantitative analysis, up to a minute concentration, of the antioxidant, as the content, can be performed in a short-time extraction operation. As described above, in the analyzing method according to this example, the extraction processing time can also be considerably shortened compared to that in the conventional method, and the antioxidant minutely included, for example, at 10 ppm, in the HDPE specimen can be rapidly analyzed.

Example 5

Figure 14:
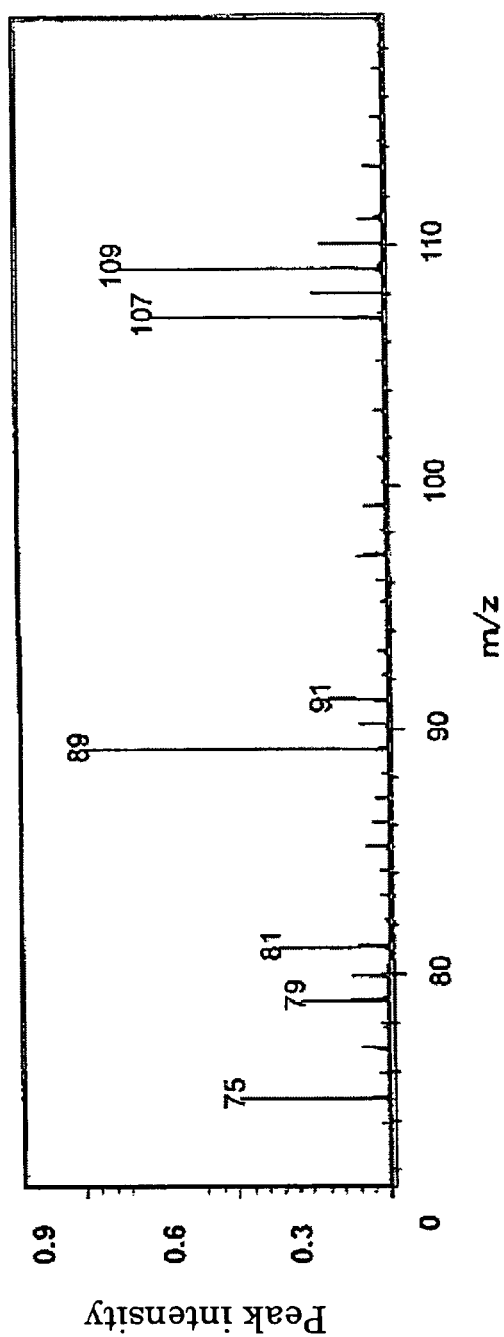
FIG. 14 is an example of the measurement results according to Example 5, a mass spectrum of an extract from a PP pellet including a brominated flame retardant in a concentration of 100 ppm.

Similarly to the method in Example 2, PP pellets including the brominated flame retardant in concentrations of 1 ppm, 10 ppm, 100 ppm, 1000 ppm, 1%, and 10% by weight were prepared as the sample pieces 1. Next, except for a silver substrate being used as the sample table 2, and extract from each PP pellet was deposited as a condensed substance on the surface of the substrate similarly to the procedure in Example 2. In this example, the deposited substance on the surface of the substrate was analyzed by time-of-flight secondary ion mass spectrometry. TRIFT2™ (manufactured by ULVAC-PHI Inc.) was used as the time-of-flight secondary ion mass spectrometry analyzer. Regarding the measurement condition, $^{69}Ga^+$ ion was used as the primary ion, the measurement mode of the secondary ion was set to the negative ion mode, the measurement range was set to m/z=1-200, and the mass resolution was set to approximately ΔM/M=5000. FIG. 14 is, as an example of the measurement results, a mass spectrum of the extract extracted from the PP pellet including the brominated flame retardant in a quantity of 100 ppm. As represented in FIG. 14, the mass-spectrum peak caused by the fragment of the bromine element was observed at m/z=79. Quantitative analysis was performed using the normalized ($^{79}Br^-/^{107}Ag^-$) peak-area ratio in which the area of the peak at m/z=79 ($^{79}Br^-$) is normalized by the area of the peak at m/z=107 ($^{107}Ag^-$) caused by the silver in the substrate.

Figure 15:
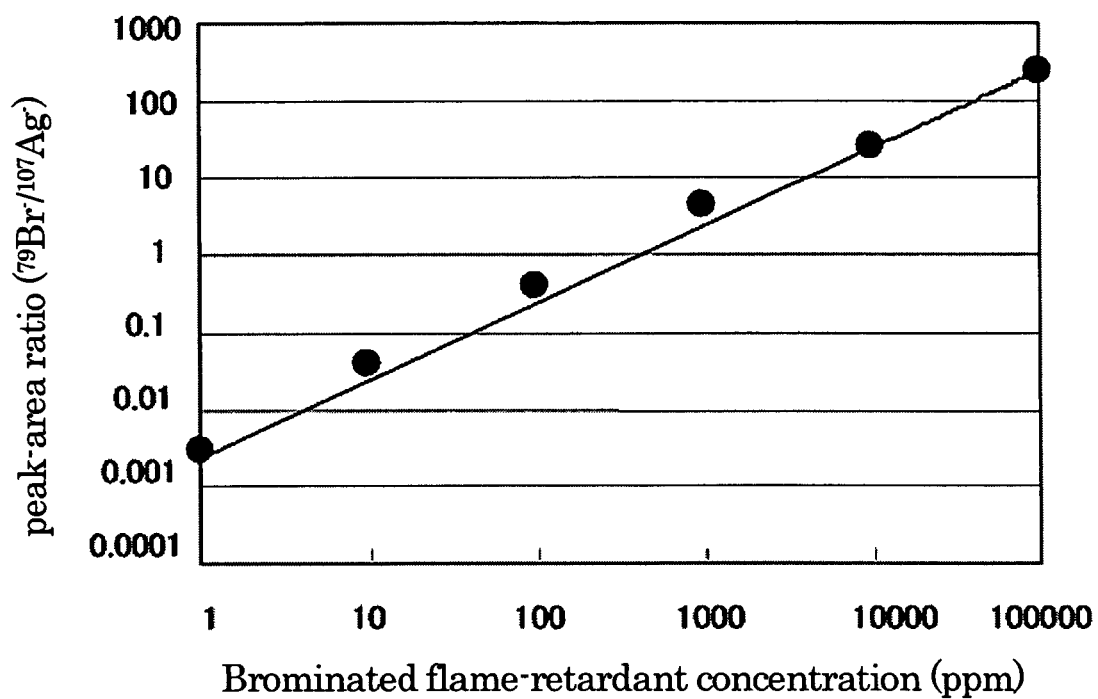
FIG. 15 is a graph representing a relationship between the mass-spectrum peak-area ratios ($^{79}Br^-/^{107}Ag^-$) obtained from an analysis in which extracts from PP pellets including a brominated flame retardant in concentrations of 1 ppm, 10 ppm, 100 ppm, 1000 ppm, 1%, and 10%, respectively, according to Example 5.

FIG. 15 is a graph representing a relationship between the mass-spectrum peak-area ratios ($^{79}Br^-/^{107}Ag^-$) obtained from the analysis of the extracts extracted from the PP pellets including the brominated flame retardant in concentrations of 1 ppm, 10 ppm, 100 ppm, 1000 ppm, 1%, and 10%. An excellent linear relationship was obtained between the brominated flame retardant concentrations and the peak-area ratios, and especially, it was found to be also detectable at a minute concentration of 1 ppm. In this example, the processing time was 10 minutes for extracting the brominated flame retardant as the content from the PP pellet of the sample piece 1; thereby, it was found that the quantitative analysis, up to such minute concentration, of the brominated flame retardant as the content can be performed by a short-time extraction operation. As described above, in the analyzing method according to this example, the extraction processing time can also be considerably shortened compared to that in the conventional method, and the brominated flame retardant minutely included, for example, in a concentration of 1 ppm, in the PP specimen, can be rapidly analyzed.

Example 6

High impact polystyrene (referred to as HIPS) specimens including brominated flame retardant as the additive in concentrations of 0.1%, 1%, and 10% by weight were prepared as the samples. H8672™ (produced by PS Japan Corp.) was used as the HIPS, and decabromodiphenylether (produced by Wako Pure Chemical Industries, Ltd.) was used as the brominated flame retardant. As the sample piece 1, the brominated flame retardant was added to and kneaded with the HIPS so that the concentrations located above; thus, pellets were prepared in which the size of the single pellet is 5 mm×3 mm×3 mm, and the weight is approximately 0.3 g. The single HIPS pellet as the sample piece 1 was mounted in contact with a silver substrate as the sample table 2, a mixed solvent of toluene and methanol (toluene/methanol=1/1 by volume) as the extraction solvent 3 of 20 µl was dropped, using the microsyringe 4, close to the HIPS pellet, so the solvent mixture was inserted into the gaps between the HIPS pellet and the silver substrate, and a process similar to the procedure represented in FIG. 2 was repeated. This solvent mixture extracts not only the HIPS but also the brominated flame retardant. Then, after 30 seconds passed from the drop operation, the HIPS pellet was removed from the silver substrate, nitrogen was blown onto the surface of the silver substrate from which the HIPS pellet was removed, and the solvent containing the brominated flame retardant was dried; thus, an extract was deposited on the surface of the silver substrate. The processing time was approximately one minute from this solvent mixture being dropped until the extract was deposited onto the surface of the silver substrate. The grades of toluene and methanol used in this example were liquid chromatography grades (produced by Wako Pure Chemical Industries, Ltd.).

Figure 16:
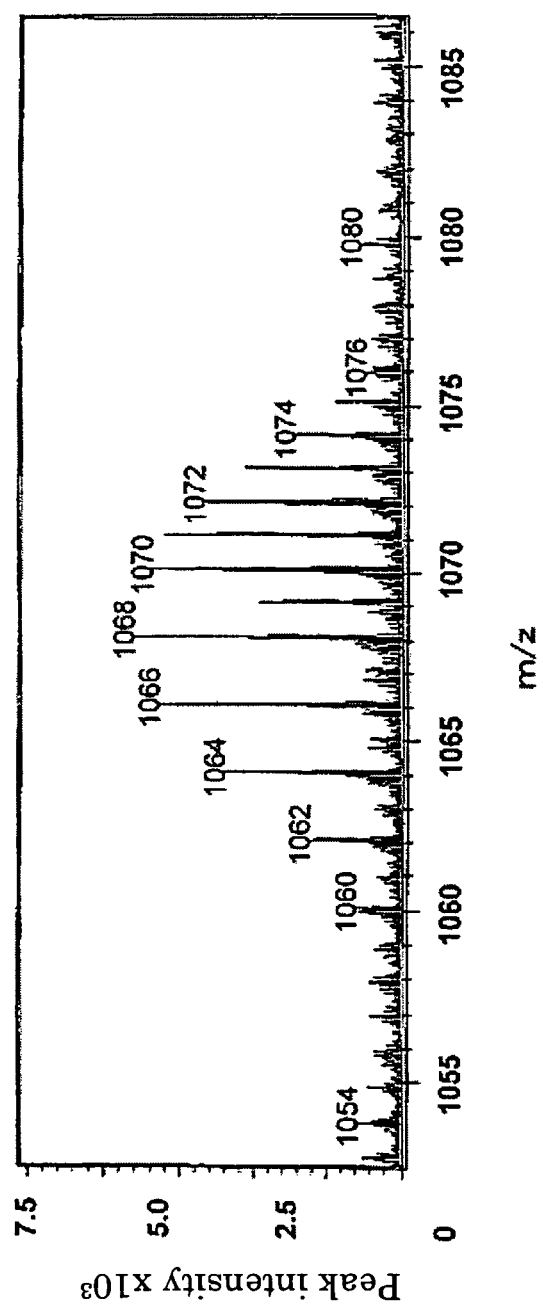
FIG. 16 is an example of the measurement results according to Example 6, and is a mass spectrum of an extract from an HIPS pellet including a brominated flame retardant in a concentration of 0.1%.

In this example, the deposited substance on the surface of the substrate was analyzed by the time-of-flight secondary ion mass spectrometry. TRIFT2™ (manufactured by ULVAC-PHI Inc.) was used as the time-of-flight secondary ion mass spectrometry analyzer. Regarding the measurement conditions, $^{69}Ga^+$ ion used as the primary ion, the measurement mode of the secondary ion was set to the positive ion mode, the measurement range was set to m/z=1-1500, and the mass resolution was set to approximately ΔM/M=5000. FIG. 16 is, as an example of the measurement results, a mass spectrum of the extract extracted from the HIPS pellet including the brominated flame retardant in a concentration of 0.1%. As represented in FIG. 16, the mass-spectrum peak caused by the peak $B^+$ due to the decabromodiphenylether as the brominated flame retardant and the peak $Ag^+$ due to the silver was observed at m/z=1068. Quantitative analysis was performed using the normalized $(^{1068}(B+Ag)^+/^{107}Ag^+)$ peak-area ratio in which the area of the peak at m/z=1068 ($^{1068}$(B+Ag)$^+$) is normalized by the area of the peak at m/z=107 ($^{107}Ag^+$). The above area ratio of the extract extracted from the HIPS pellet including the brominated flame retardant in a concentration of 0.1% was 0.005.

Figure 17:
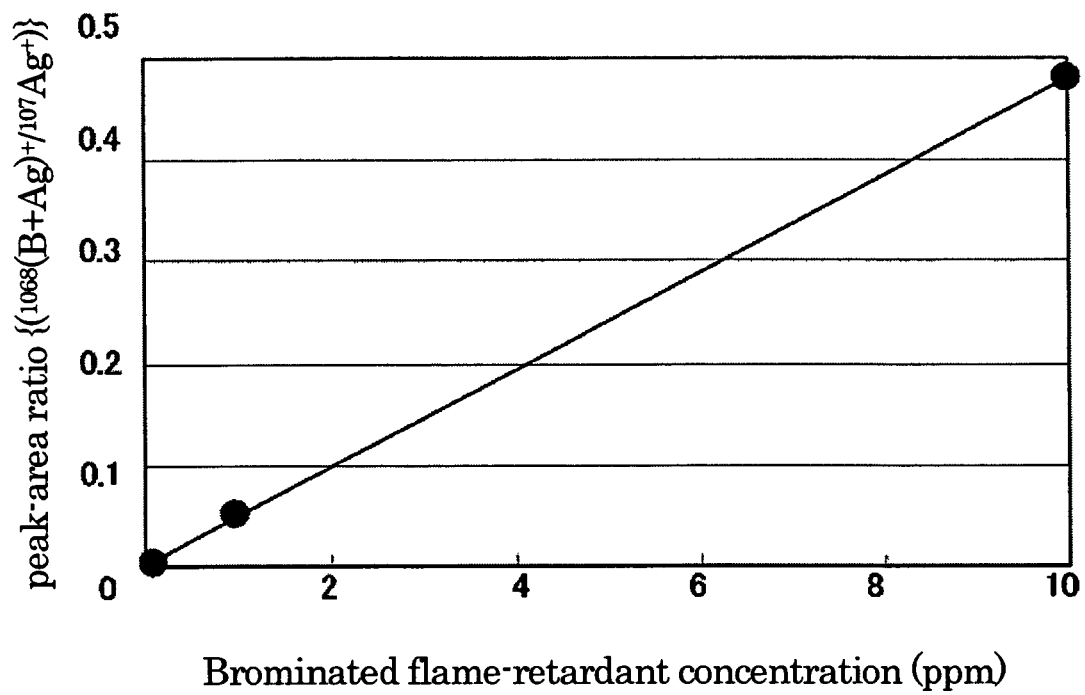
FIG. 17 is a graph representing a relationship between the mass-spectrum peak-area ratios ($^{1068}(B+Ag)^+/^{107}Ag^+$) obtained from an analysis of extracts from HIPS pellets including a brominated flame retardant in concentrations of 0.1%, 1%, and 10%, respectively, according to Example 6.

FIG. 17 is a graph representing a relationship between the mass-spectrum peak-area ratios $(^{1068}(B+Ag)^+/^{107}Ag^+)$ obtained from the analysis of the extracts being extracted from the HIPS pellets including the brominated flame retardant in concentrations of 0.1%, 1%, and 10%. An excellent linear relationship was obtained between the brominated flame retardant concentrations and the peak-area ratios. In this example, the processing time was 1 minute for extracting the brominated flame retardant as the content from the HIPS pellet; thus, it was determined that the quantitative analysis, up to the minute concentration of the brominated flame retardant as the content, can be performed by an extremely short-time extraction operation. As described above, in the analyzing method according to this example, the extraction processing time can be considerably shortened compared to that in the conventional method, and content included in a matrix that is soluble in a solvent used in extracting the content, such as the brominated flame retardant included in the HIPS specimen, can also be rapidly analyzed.

Example 7

Figure 18:
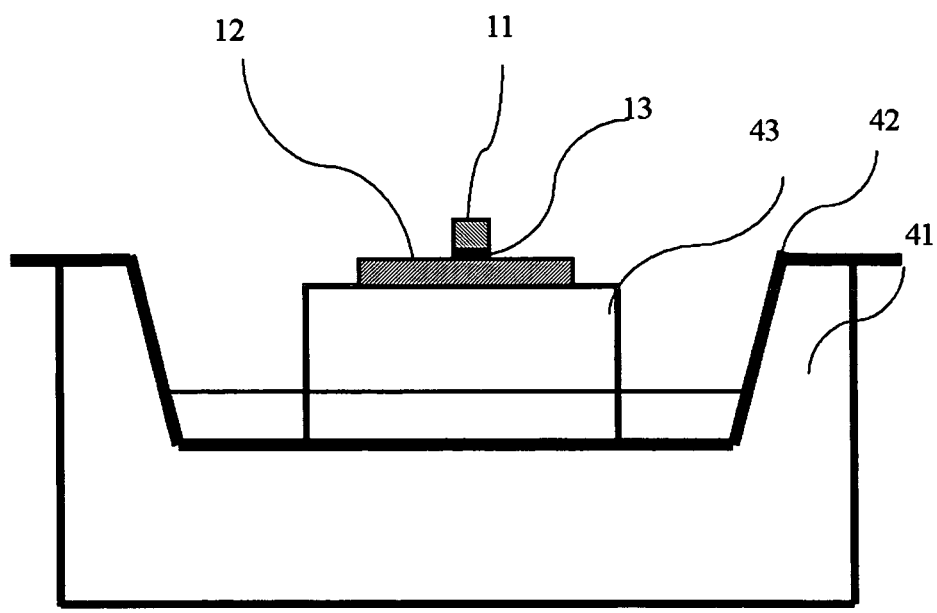
FIG. 18 is a view representing a state in which content is extracted from a sample piece according to Example 7.

In this example, similarly to the method in Example 4, an HDPE pellet including the antioxidant in a concentration of 500 ppm by weight was prepared. This HDPE pellet as the sample piece 1 was mounted in contact with a silicon substrate as the sample table 2; then, similarly to the method in Example 4, chloroform as the extraction solvent 3 was dropped and inserted into the gaps between the HDPE pellet and the silicon substrate. Then, by processing for 12 minutes, similarly to the procedure in Example 4, the antioxidant was extracted into the solvent, and this antioxidant as the extract was deposited as a condensed substance onto the surface of the substrate. FIG. 18 is a view representing a state in which the content is extracted from the sample piece according to this example. As represented in FIG. 18, a support 43 is placed inside a washing bath 42, into which ion exchanged water is put, in an ultrasonic washer 41, and a silicon substrate 12 is mounted on the support 43. An HDPE pellet 11 is mounted in contact with the top face of this silicon substrate 12, and chloroform 13 is maintained in the gaps between the top face of the silicon substrate 12 and the HDPE pellet 11. Thus, in this example, during extraction processing, ultrasonic vibration, for example, at a frequency of 45 kHz, is added to the HDPE pellet 11, the chloroform 13, and the silicon substrate 12. The ultrasonic washer used in this example is Branson Series Type 2510J-DTAT™ (manufactured by Yamato Scientific Co., Ltd.).

Figure 19:
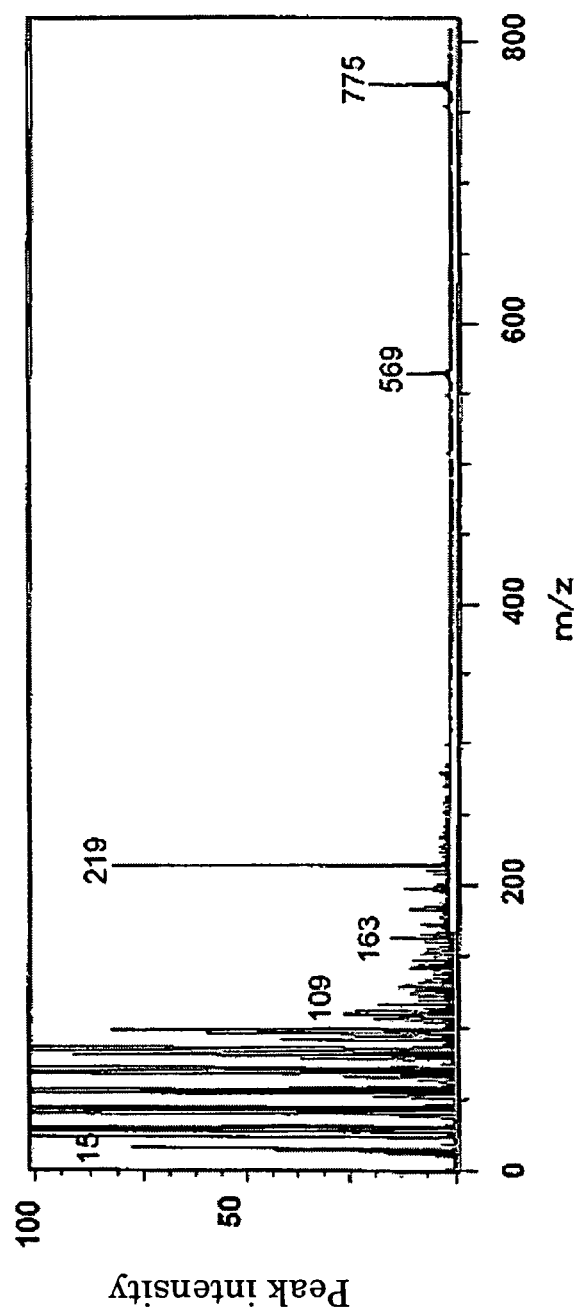
FIG. 19 is a mass spectrum of an extract, obtained by the method according to Example 7, extracted from an HDPE pellet including an antioxidant in a concentration of 500 ppm.

Similarly to the method in Example 4, the deposited substance was analyzed by time-of-flight secondary ion mass spectrometry. FIG. 19 is a mass spectrum of the extract, obtained by the method according to this example, extracted from the HDPE pellet including the antioxidant in a quantity of 500 ppm. As represented in FIG. 19, the mass peak due to the antioxidant was observed at m/z=775. The normalized $(^{775}M^+/^{28}Si^+)$ area ratio in which the area of the peak at m/z=775 ($^{775}M^+$) is normalized by the area of the peak at m/z=28 ($^{28}Si^+$) caused by the silicon in the substrate was 25, which is five times larger than that of Example 4 in which the ultrasonic waves were not added during the extraction operation. That is, by adding the ultrasonic waves, the extract amount of the antioxidant was increased. In the method according to this example, because the extract content is increased, in response to a material in which the amount of content to be analyzed is further minute, the content can also be accurately analyzed in a short time.

Embodiment 8

Figure 20:
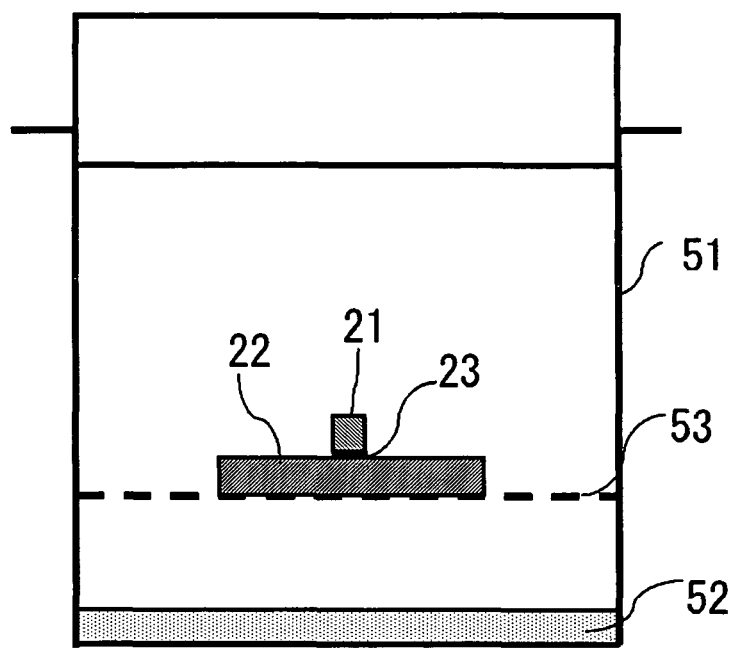
FIG. 20 is a view representing a state according to Example 8, in which content is extracted from a sample piece.

In this example, similarly to the procedure in Example 5, a PP pellet as the sample piece 1 including a brominated flame retardant in a concentration of 100 ppm by weight was prepared. This pellet was mounted in contact with a silver substrate as the sample table 2; then, similarly to the procedure in Example 5, toluene as the extraction solvent 3 was dropped and inserted into the gaps between the PP pellet and the silver substrate. The sample piece was kept for 10 minutes with the toluene maintained in the gaps between the PP pellet and the silver substrate; thereby, the brominated flame retardant was extracted into the toluene, so that the brominated flame retardant was deposited on to the silver substrate as a condensed substance. FIG. 20 is a view representing a state according to this example, in which the content is extracted from the sample piece. As represented in FIG. 20, during the extraction operation, a silver substrate 22, on which a PP pellet 21 is mounted, and between which and the PP pellet 21 toluene 23 is maintained, is placed inside a sealed container 51 in which toluene vapor is saturated. Specifically, toluene 52 that generates vapor is contained at the bottom of this sealed container 51, and a shelf plate 53 having holes is provided on the upper side of the toluene 52 that generates vapor. The silver substrate 22 is placed on the top face of this shelf plate 53, the PP pellet 21 is mounted in contact with the top face of this silver substrate 22, and the toluene 23 is maintained in the gaps between the top face of the silver substrate 22 and the PP pellet 21. That is, because the PP pellet 21 is stored in saturated vapor of toluene during the operation in which the brominated flame retardant is extracted from the PP pellet 21, loss, due to vaporization, of the toluene 23 is prevented; therefore, the re-dropping of the toluene 23 becomes unnecessary, and the analysis process becomes simple. After the extraction, the silver substrate was taken out from the sealed container 51, the PP pellet 21 was removed from the silver substrate 22, and the solvent was dried with nitrogen blown onto the surface of the silver substrate 22, so that the brominated flame retardant was deposited on the surface of the silver substrate 22 as a condensed substance.

Figure 21:
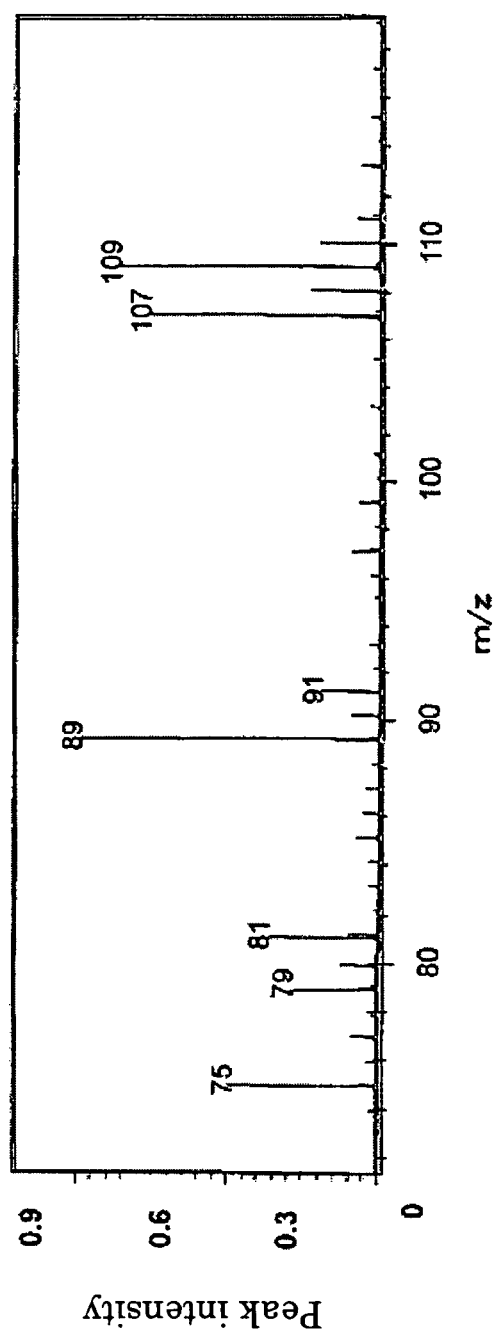
FIG. 21 is a mass spectrum of an extract, obtained by the method according to Example 8, extracted from a PP pellet including a brominated flame retardant in a concentration of 100 ppm.

In this example, similarly to the method in Example 5, the deposited substance on the surface of the substrate was analyzed by time-of-flight secondary ion mass spectrometry. FIG. 21 is a mass spectrum of the extract, obtained by the method according to this example, extracted from the PP pellet including the brominated flame retardant in a concentration of 100 ppm. As represented in FIG. 21, a mass spectrum peak due to the bromine was observed at m/z=79. Quantitative analysis of the brominated flame retardant included in the PP pellet could be performed using the normalized ($^{79}Br^-/^{107}Ag^-$) peak area ratio that is obtained from the area of the peak at m/z=79 ($^{79}Br^-$), normalized by the area of the peak at m/z=107 ($^{107}Ag^-$) caused by the silver in the substrate. That is, in the method according to this example, not only the extraction processing time can be considerably shortened compared to that in the conventional method, but also the re-dropping of the extraction solvent becomes unnecessary; moreover, because of the simple process, the brominated flame retardant as the content included in the PP specimen can be rapidly analyzed.

Example 9

In this example, similarly to the procedure in Example 6, an HIPS pellet including the brominated flame retardant in a concentration of 0.1% by weight was prepared. In this example, except for a solvent mixture of toluene and methanol (toluene/methanol=1/1 by volume) saturated with silver perchlorate being used as the extraction solvent 3, similarly to the procedure in Example 6, an extract from the HIPS pellet was deposited as a condensed substance on the surface of the silver substrate.

Figure 22:
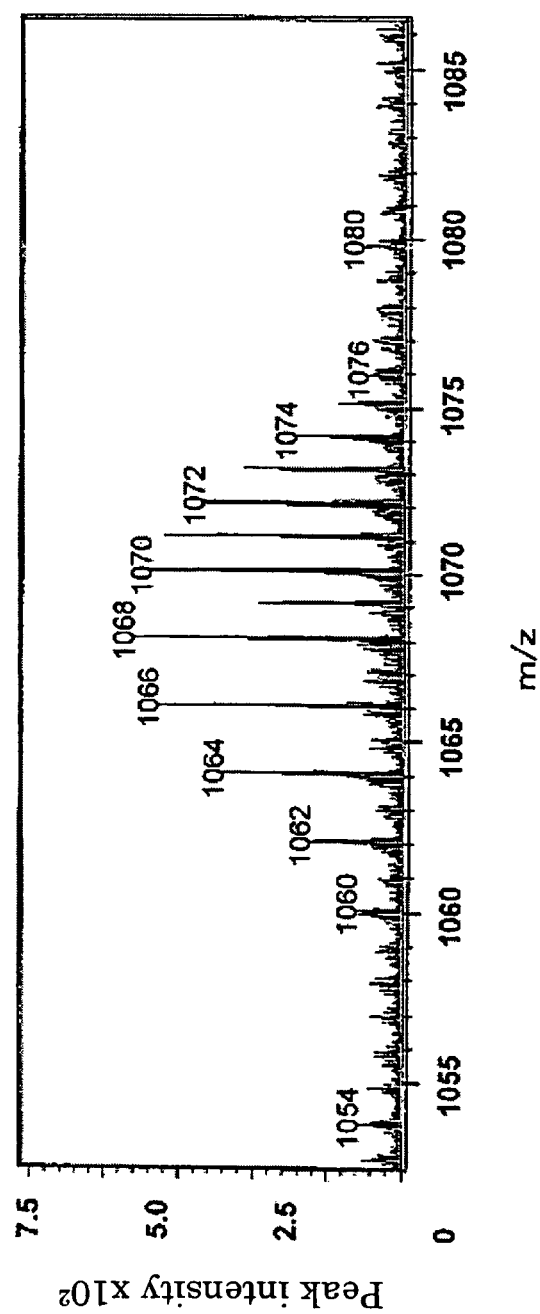
FIG. 22 is a mass spectrum of an extract, obtained by a method according to Example 9, extracted from an HIPS pellet including a brominated flame retardant in a quantity of 0.1%.
Figure 23:
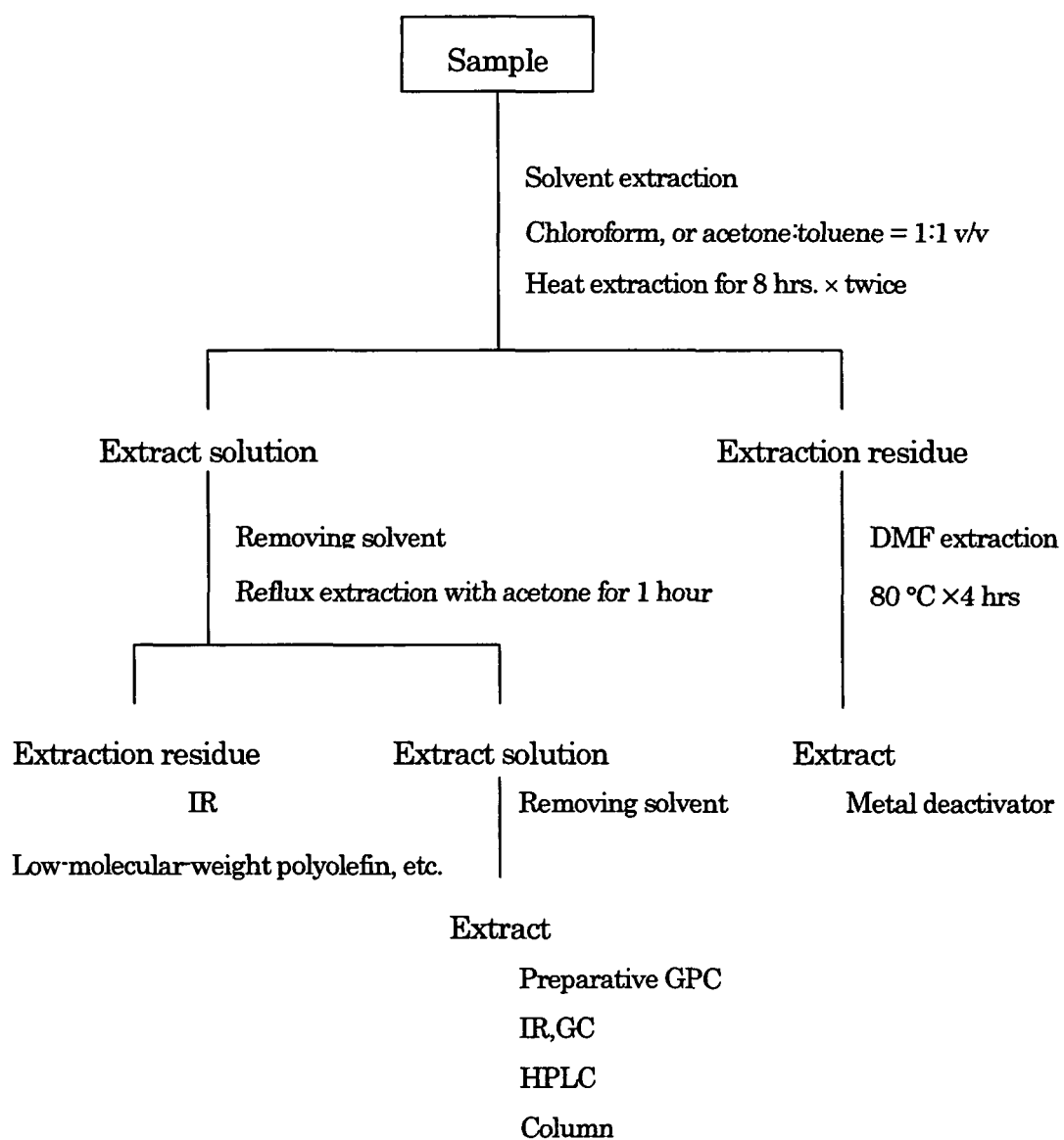
FIG. 23 is a flowchart representing a conventional method of analyzing an additive included in a polyolefin resin.

In this example, similarly to the method in Example 6, the deposited substance on the surface of the substrate was analyzed by time-of-flight secondary ion mass spectrometry. FIG. 22 is a mass spectrum of the extract, obtained by the method according to this example, extracted from the HIPS pellet including the brominated flame retardant in a concentration of 0.1%. As represented in FIG. 22, the mass spectrum peak due to the decabromodiphenylether as brominated flame retardant and silver was observed at m/z=1068. The normalized ($^{1068}(B+Ag)^+/^{107}Ag^+$) peak area ratio in which the area of the peak at m/z=1068 ($^{1068}(B+Ag)^+$) is normalized to the area of the peak at m/z=107 ($^{107}Ag^+$) caused by the silver in the substrate was 0.05, which is ten times larger than that of Example 6 in which silver perchlorate, a conductive substance, is not added. That is, in the method according to this example, compared to the conventional method, not only the extraction processing time can be considerably shortened, but also the sensitivity for analyzing the extract is remarkably improved; consequently, the brominated flame retardant as the content included in the HIPS specimen can be rapidly analyzed.

INDUSTRIAL APPLICABILITY

The method of analyzing a minute content according to the present invention can be used for analyzing a minute content, such as an additive, included in a polymer material such as plastics, rubber, adhesives, encapsulating resins, or molding resins. Moreover, a minute content included in a polymer material constituting a case, a molded product, and a printed wiring board, that are manufactured using the polymer material, can be analyzed.

What is claimed is:

1. A method of determining a previously unknown concentration of a known additive material in a polymer material by analyzing a plurality of samples of the polymer material containing respective known concentrations of the additive material, the method comprising:

placing a pellet of one of the samples of the polymer material containing one of the known concentrations of the additive material, the additive material being different from the polymer material, on a face of a substrate, wherein the face of the substrate is one of silver and gold;

disposing an organic solvent, which dissolves the additive material contained in the pellet of the polymer material, on the pellet of the polymer material and between the face of the substrate and the pellet of the polymer material;

maintaining the organic solvent between the face of the substrate and the pellet of the polymer material at room temperature and dissolving some of the additive material from the pellet of the polymer material in the organic solvent;

removing the pellet of the polymer material from the face of the substrate, leaving a residue of the additive material that has been dissolved in the organic solvent on the face of the substrate;

subjecting the residue of the additive material that has been left on the face of the substrate to time-of-flight secondary ion mass spectrometry and correlating results of the time-of-flight secondary mass spectrometry with the known concentration of the additive material of the one of the samples of the polymer material that has been analyzed; and repeating the foregoing steps for each of the samples of the polymer material with known concentrations of the additive material and producing a relationship between the results of the time-of-flight secondary ion mass spectrometry for the samples of the polymer material and concentrations of the additive material in the samples of the polymer material with the known concentrations, for determination of the previously unknown concentration of the additive material in the polymer material.

2. The method as recited in claim 1, including vibrating the substrate while maintaining the organic solvent between the face of the substrate and the pellet of the polymer material and dissolving some of the additive material in the organic solvent, and maintaining the organic solvent at room temperature.

3. A method of determining a previously unknown concentration of decabromodiphenylether in polystyrene by analyzing a plurality of samples of the polystyrene containing respective known concentrations of decabromodiphenylether, the method comprising:

placing a pellet of one of the samples of polystyrene containing one of the known concentrations of decabromodiphenylether, as a flame retardant, on a silver face of a substrate;

disposing a mixture of toluene and methanol, which dissolves polystyrene and decabromodiphenylether, on the pellet of polystyrene and between the pellet of polystyrene and the silver face of the substrate;

maintaining the mixture of toluene and methanol between the silver face of the substrate and the pellet of polystyrene and dissolving some of the polystyrene and the decabromodiphenylether in the mixture of toluene and methanol;

removing the pellet of polystyrene from the silver face of the substrate, leaving a residue of the polystyrene and the decabromodiphenylether that has been dissolved in the mixture of toluene and methanol on the silver face of the substrate;

subjecting the residue of polystyrene and decabromodiphenylether that has been left on the silver face of the substrate to time-of-flight secondary ion mass spectrometry and correlating results of the time-of-flight secondary mass spectrometry with the known concentration of the decabromodiphenylether in the polystyrene of the one of the samples of polystyrene that has been analyzed; and repeating the foregoing steps for each of the samples of polystyrene with known concentrations of decabromodiphenylether and producing a relationship between the results of the time-of-flight secondary ion mass spectrometry for the samples of polystyrene and concentrations of decabromodiphenylether in the samples of polystyrene with the known concentrations, for determination of the previously unknown concentration of decabromodiphenylether in polystyrene.

4. The method as recited in claim 3, wherein the mixture of toluene and methanol includes silver perchlorate dissolved in the mixture to saturation.

5. A method of determining a previously unknown concentration of decabromodiphenylether in polypropylene by analyzing a plurality of samples of the polystyrene containing respective known concentrations of decabromodiphenylether, the method comprising:

placing a pellet of one of the samples of polypropylene containing one of the known concentrations of decabromodiphenylether, as a flame retardant, on a silver face of a substrate;

disposing toluene, which dissolves decabromodiphenylether, on the pellet of polypropylene and between the pellet of polypropylene and the silver face of the substrate;

maintaining the toluene between the silver face of the substrate and the pellet of polypropylene and dissolving some of the decabromodiphenylether in the toluene;

removing the pellet of polypropylene from the silver face of the substrate, leaving a residue of the decabromodiphenylether that has been dissolved in the toluene on the silver face of the substrate;

subjecting the residue of decabromodiphenylether that has been left on the silver face of the substrate to time-of-flight secondary ion mass spectrometry and correlating results of the time-of-flight secondary mass spectrometry with the known concentration of the decabromodiphenylether in the polypropylene of the one of the samples of polystyrene that has been analyzed; and repeating the foregoing steps for each of the samples of polypropylene with known concentrations of decabromodiphenylether and producing a relationship between the results of the time-of-flight secondary ion mass spectrometry for the samples of polypropylene and concentrations of decabromodiphenylether in the samples of polypropylene with the known concentrations, for determination of the previously unknown concentration of decabromodiphenylether in polypropylene.

* * * * *